US012740927B2

(12) United States Patent
Kim et al.

(10) Patent No.: US 12,740,927 B2
(45) Date of Patent: Sep. 22, 2026

(54) MIXED SURFACTANT FOR PREPARING TRANSPARENT MICROEMULSION AND FINE NANOEMULSION, AND COSMETIC COMPOSITION PREPARED USING THE SAME

(71) Applicant: BIOBEAUTECH Co., Ltd., Seongnam-si (KR)

(72) Inventors: In Young Kim, Seongnam-si (KR); Jae Young Yeon, Yongin-si (KR)

(73) Assignee: BIOBEAUTECH CO., LTD., Seongnam-si (KR)

( * ) Notice: Subject to any disclaimer, the term of this patent is extended or adjusted under 35 U.S.C. 154(b) by 267 days.

(21) Appl. No.: 18/606,039

(22) Filed: Mar. 15, 2024

(65) Prior Publication Data

US 2025/0073146 A1 Mar. 6, 2025

(30) Foreign Application Priority Data

Sep. 1, 2023 (KR) ........................ 10-2023-0116230

(51) Int. Cl.

| | |
|---|---|
| ***A61K 8/39*** | (2006.01) |
| ***A61K 8/06*** | (2006.01) |
| ***A61K 8/60*** | (2006.01) |
| ***A61Q 19/00*** | (2006.01) |

(Continued)

(52) U.S. Cl.

CPC ................ *A61K 8/39* (2013.01); *A61K 8/068* (2013.01); *A61K 8/604* (2013.01); *A61Q 19/007* (2013.01); *A61Q 19/02* (2013.01); *A61Q 19/08* (2013.01); *A61K 2800/21* (2013.01); *A61K 2800/262* (2013.01); *A61K 2800/596* (2013.01)

(58) Field of Classification Search

CPC .... A61K 9/0014; A61K 9/1075; A61K 31/05; A61K 31/658; A61K 47/14; A61K 47/44; A61K 31/352; A61K 9/0095; A61K 9/127; A61K 2300/00; A61K 31/4155; A61K 47/22; A61K 47/24; A61K 47/28; A61K 8/39; A61K 8/9789; A61K 9/1277; A61K 2800/262; A61K 47/06; A61K 47/10; A61K 47/12; A61K 9/10; A61K 9/1272; A61K 9/145; A61K 9/19; A61K 2800/5922; A61K 31/192; A61K 45/06; A61K 8/062; A61K 8/375; A61K 8/604; A61K 8/92; A61K 8/9794; A61K 2800/21; A61K 2800/30; A61K 2800/49; A61K 2800/596; A61K 31/501; A61K 31/519; A61K 31/7048; A61K 36/185; A61K 36/3482; A61K 36/81; A61K 8/068; A61K 8/37; A61K 8/4973; A61K 8/86; A61K 8/922; A61K 9/16; A61K 9/501; A61K 9/5089; A61K 9/5123; A61K 2800/244; A61K 2800/412; A61K 2800/413; A61K 2800/52; A61K 31/01; A61K 31/015; A61K 31/12; A61K 31/202; A61K 31/23; A61K 31/381; A61K 31/415; A61K 31/425; A61K 31/515; A61K 31/575; A61K 31/593; A61K 31/685; A61K 33/06; A61K 33/30; A61K 36/071; A61K 36/28; A61K 36/3486; A61K 36/484; A61K 36/67; A61K 36/73; A61K 36/82; A61K 36/896; A61K 47/02; A61K 47/26; A61K 47/32; A61K 47/38; A61K 8/0208; A61K 8/0216; A61K 8/31; A61K 8/345; A61K 8/44; A61K 8/442; A61K 8/4953; A61K 8/60; A61K 8/602; A61K 8/63; A61K 8/671; A61K 8/676; A61K 8/73; A61K 8/731; A61K 8/735; A61K 8/8111; A61K 8/927; A61K 8/9711; A61K 8/9728; A61K 8/9741; A61K 8/99; A61K 9/0019; A61K 9/0053; A61K 9/0056; A61K 9/006; A61K 9/0078; A61K 9/1271; A61K 9/1664; A61K 9/2054; A61K 9/2846; A61K 9/2853; A61K 9/4816; A61K 9/5115; A61K 9/5161; A61K 9/5176; A61K 8/06; A61K 8/675; A61K 8/342; A61K 8/347; A61K 8/368; A61K 8/416; A61K 2800/22; A61K 33/00; A61K 47/20; A61K 47/36; A61K 8/22; A61K 8/315; A61K 9/06; A61K 9/1617; A61K 9/4858; A61K 8/046; A61K 8/466; A61K 8/553; A61K 8/85

See application file for complete search history.

(56) References Cited

FOREIGN PATENT DOCUMENTS

| | | | |
|---|---|---|---|
| KR | 10-0182399 | B1 | 5/1999 |
| KR | 10-0452165 | B1 | 10/2004 |
| KR | 10-1668911 | B1 | 10/2016 |

(Continued)

OTHER PUBLICATIONS

KR20220056515A translation (Year: 2022).*

Korean Office Action for KR 10-2023-0116230 dated Oct. 23, 2023.

*Primary Examiner* — Audrea B Coniglio

(74) *Attorney, Agent, or Firm* — Sughrue Mion, PLLC

(57) ABSTRACT

Disclosed are a mixed surfactant for preparing a transparent microemulsion and a fine nanoemulsion without using a certain high-pressure microfluidizer. A transparent microemulsion can be prepared only by simple stirring in a ternary component system formed by adding an oil and purified water to the surfactant mixture. In addition, a nanoemulsion can be prepared in the ternary component system under simple conditions. The microemulsion is applicable to various cosmetics, can be absorbed quickly in the skin and exhibits excellent skin improvement effects such as moisturizing, fine wrinkle alleviation, and whitening and lifting improvement effects.

2 Claims, 17 Drawing Sheets

(51) Int. Cl.
*A61Q 19/02* (2006.01)
*A61Q 19/08* (2006.01)

(56) References Cited

FOREIGN PATENT DOCUMENTS

| | | | | | |
|---|---|---|---|---|---|
| KR | 10-1733376 | B1 | | 5/2017 | |
| KR | 10-1744137 | B1 | | 6/2017 | |
| KR | 10-1827611 | B1 | | 2/2018 | |
| KR | 10-1878941 | B1 | | 7/2018 | |
| KR | 10-2056116 | B1 | | 12/2019 | |
| KR | 10-2022-0056515 | A | | 5/2022 | |
| KR | 20220056515 | A | * | 5/2022 | ............... A61K 8/06 |

* cited by examiner mixing 10% of transparent microemulsion with distilled water

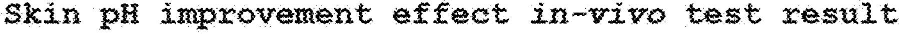
FIG. 17
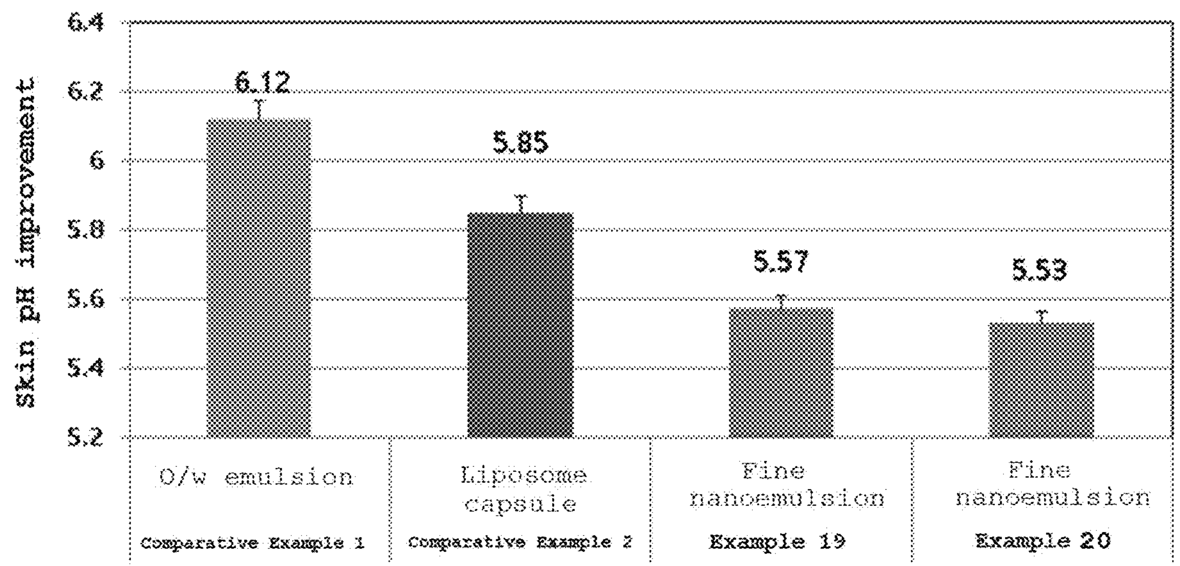

MIXED SURFACTANT FOR PREPARING TRANSPARENT MICROEMULSION AND FINE NANOEMULSION, AND COSMETIC COMPOSITION PREPARED USING THE SAME

CROSS-REFERENCE TO RELATED APPLICATIONS

This application claims priority to Korean Patent Application No. 10-2023-0116230 filed Sep. 1, 2023, the entire disclosures of which are incorporated herein by reference.

BACKGROUND OF THE INVENTION

Field of the Invention

The present invention relates to a mixed surfactant for preparing a transparent microemulsion and a fine nanoemulsion without using a certain high-pressure microfluidizer, and a cosmetic composition prepared using the same.

Description of the Related Art

A general method of preparing a liposome or nanoemulsion in the cosmetics industry includes stirring a mixture of oil and water using hydrogenated lecithin as a surfactant and then allowing the mixture to pass through a high-pressure microfluidizer (1 to 6 times) to obtain the nanoemulsion.

Recently, there has been actively reported research on phenomena occurring at the interface related to the formation of irregular emulsified particles on the micron (μm) scale that occur in a mixed system of a surfactant, an oil, and water. It has been reported that regions where cubic phase, hexagonal phase, and multilayered lamellar structures are formed can be optionally obtained through a three-phase system (general term for the surfactant: oil (oil phase): water (aqueous phase)) under predetermined conditions. In particular, there are known many cases in which monovesicular or multilayer lamellar vesicles are formed in mixed systems using hydrogenated lecithin.

Methods of preparing nanoemulsions or forming transparent microemulsions in the conventional three-phase surfactant system are disadvantageously very difficult. To solve this disadvantage, it is important to develop surfactants and there is a need for development of methods that are capable of preparing nanoemulsions from lipophilic substances by simply stirring oil and aqueous phases in the presence of a surfactant, and methods that are capable of preparing transparent microemulsions.

PRIOR ART LITERATURE

Patent Document (Patent Document 1) Korean Patent No. 0182399 (Dec. 11, 1998)

(Patent Document 2) Korean Patent No. 1668911 (Oct. 18, 2016)

SUMMARY OF THE INVENTION

In order to solve the problems of the prior art as described above, it is one object of the present invention to provide a surfactant for producing transparent microemulsions by simple stirring and fine nanoemulsions by simple operation.

In addition, it is another object of the present invention to provide a cosmetic composition such as skin toner, lotion, cream, essence, ampoule, or mask sheet containing the transparent microemulsion and the fine nanoemulsion.

In accordance with one aspect of the present invention, provided is a mixed surfactant for preparing an emulsion, the mixed surfactant containing sucrose distearate and polyglyceryl-10 oleate.

In accordance with another aspect of the present invention, provided is an emulsion prepared by mixing a mixed surfactant containing sucrose distearate and polyglyceryl-10 oleate with an oily phase and an aqueous phase, followed by stirring.

In an embodiment, the emulsion may be a transparent emulsion or a nanoemulsion.

In accordance with another aspect of the present invention, provided is a cosmetic composition containing the emulsion according to the present invention.

In accordance with another aspect of the present invention, provided is a nanoemulsion prepared by diluting the transparent emulsion according to the present invention in an aqueous phase.

In accordance with another aspect of the present invention, provided is a cosmetic composition containing the nanoemulsion according to the present invention.

BRIEF DESCRIPTION OF THE DRAWINGS

The above and other objects, features and other advantages of the present invention will be more clearly understood from the following detailed description taken in conjunction with the accompanying drawings, in which:

FIG. 17 is a graph showing the skin pH improvement effect of the fine nanoemulsion according to an embodiment of the present invention.

DETAILED DESCRIPTION OF THE INVENTION

Figure 1:
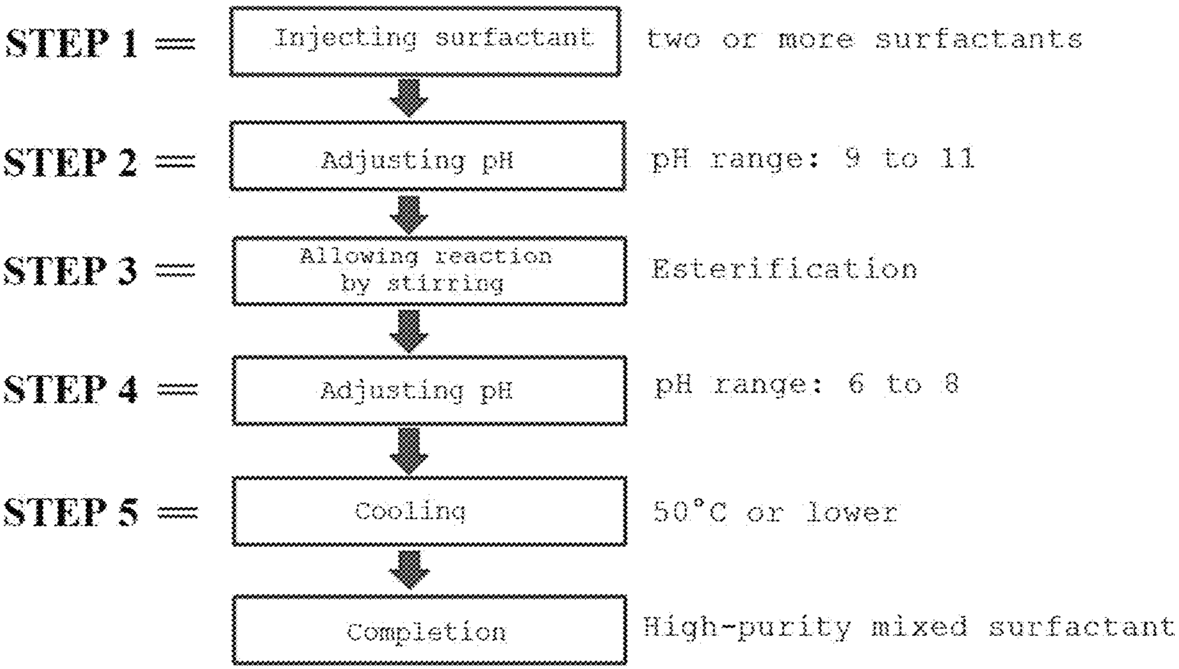
FIG. 1 illustrates a process for preparing a mixed surfactant according to the present invention.

Hereinafter, the present invention will be described in more detail with reference to the annexed drawings.

Microemulsions and nanoemulsions can be prepared by simple mixing and stirring the mixed surfactant according to the present invention without using a certain high-pressure microfluidizer. The microemulsion prepared herein was a transparent microemulsion and the nanoemulsion prepared herein was a fine nanoemulsion.

According to the method for preparing transparent microemulsions and fine nanoemulsions according to the present invention, transparent microemulsions or fine nanoemulsions can be prepared by selecting a high-purity mixed surfactant and an oil, and adding an aqueous phase mixed with purified water or glycerin thereto.

Based on this research, the present invention provides a mixed surfactant for preparing an emulsion containing sucrose distearate and polyglyceryl-10 oleate.

Meanwhile, the present invention is an emulsion prepared by mixing the mixed surfactant containing sucrose fatty acid ester and polyglyceryl-10 fatty acid ester, an oil phase and an aqueous phase, followed by stirring.

By controlling the addition ratio of the mixed surfactant, the oil phase, and the aqueous phase, the emulsion of the present invention may be prepared as a transparent microemulsion or nanoemulsion. In particular, the addition ratio of the aqueous phase may greatly affect preparation of the microemulsion or nanoemulsion.

Meanwhile, the present invention provides a nanoemulsion prepared by diluting the transparent microemulsion of the present invention in an aqueous phase. When the microemulsion prepared according to the present invention is diluted in the aqueous phase, it can be easily phase-changed to the nanoemulsion. Another feature of the present invention is that phase change can be achieved through such a simple operation.

Meanwhile, the present invention provides a cosmetic composition containing the emulsion, the microemulsion or the nanoemulsion of the present invention.

The emulsion of the present invention may be used in skin toners, lotions, emulsions, creams, essences, ampoules or mask sheets, and the like to facilitate percutaneous absorption of useful substances and provide excellent effects on the skin of obtaining moisturizing effects, supplying nutrition, adjusting pH, controlling skin oil-moisture balance, alleviating fine wrinkles, and improving whitening and lifting effects.

The preferred embodiments of the present invention will be described in detail for illustrative purposes and those skilled in the art will appreciate that various modifications, additions and substitutions are possible, without departing from the scope and spirit of the invention as disclosed in the accompanying claims.

Hereinafter, embodiments according to the present invention will be described in detail with reference to the attached drawings. Identical or corresponding reference numerals refer to like elements throughout the description of the figures and redundant description thereof will be omitted.

The terms used in the present invention are as follows.

Sucrose, oleic acid, stearic acid, polyglyceryl-10, polyglyceryl-2, fine nanoemulsion, transparent microemulsion, lamellar structure, hexagonal phase (H), cubic phase (Q1), reverse micelle, surfactant phase, sucrose distearate, sucrose distearate, polyglyceryl-10 dioleate, polyglyceryl-10 oleate, polyglyceryl-10 distearate, polyglyceryl-10 stearate, polyglyceryl-2 dioleate, polyglyceryl-2 oleate, oil-in-water (O/W) emulsion, water-in-oil (W/O) emulsion, skin toner, lotion emulsion, essence, ampoule, mask sheet, paddle mixer, homo-mixer, moisturizing effect, pH control, citric acid, oil water balance, skin lifting effect.

General terms not mentioned above will follow the nomenclature of commonly known chemical and cosmetic dictionaries.

Examples 1 to 7: Preparation of Mixed Surfactant Composition

According to one embodiment of the present invention, the composition of a surfactant that can be used to prepare a microemulsion or nanoemulsion without using a special high-pressure microfluidizer is summarized in Table 1 below.

TABLE 1

| Compositions of Examples 1 to 7 | | | | | | | |
|---|---|---|---|---|---|---|---|
| Component name | Example 1 (wt %) | Example 2 (wt %) | Example 3 (wt %) | Example 4 (wt %) | Example 5 (wt %) | Example 6 (wt %) | Example 7 (wt %) |
| Sucrose distearate | 30 | 30 | | | | | 7.5 |
| Sucrose dioleate | | | 30 | 30 | | | 7.5 |
| Polyglyceryl-10 stearate | 70 | | | 70 | | 35 | 35 |
| Polyglyceryl-10 oleate | | 70 | 70 | | 70 | 35 | 35 |
| Polyglyceryl-2 stearate | | | | | | 15 | 7.5 |
| Polyglyceryl-2 oleate | | | | | 30 | 15 | 7.5 |
| Total | 100 | 100 | 100 | 100 | 100 | 100 | 100 |

As shown in Examples 1 to 7, two or more of sucrose distearate, sucrose dioleate, polyglyceryl-10 stearate, polyglyceryl-10 oleate, polyglyceryl-2 stearate, and polyglyceryl-2 oleate were injected into a reaction tank, the pH was adjusted to a range of 9 to 11 (optimal pH of 9.7), the components were mixed while stirring at 120 to 180° C. for 2 to 4 hours in the presence of nitrogen gas to remove unreacted fatty acids, and the mixture was homogeneously dispersed and mixed.

The resulting mixture was adjusted again to pH 6 to 8 (optimal pH of 6.9), further stirred for 2 hours at 110 to 160° C., and cooled to 50° C. or lower to prepare a mixed surfactant composition of the present invention.

This method will be described in more detail with reference to Example 2. 5 to 40% by weight of sucrose distearate and 40 to 90% by weight of polyglyceryl-10 oleate were mixed, pH was adjusted within the range of 9 to 11 (optimum pH of 9.7), the resulting mixture was stirred for 2 to 4 hours at 120 to 180° C. in the presence of nitrogen gas to remove unreacted substances and the mixture was homogeneously dispersed. The resulting mixture was again adjusted in pH within the range of 6 to 8 (optimal pH of 6.9), further stirred for 2 hours at 110 to 160° C., and cooled to 50° C. or less to complete the preparation.

This method will be described in more detail with reference to Example 2. 30% by weight of sucrose distearate and 70% by weight of polyglyceryl-10 oleate were mixed in the same manner as above to obtain a mixed surfactant enabling preparation of both transparent microemulsions and fine nanoemulsions.

FIG. 1 illustrates a process for preparing the mixed surfactant of the present invention.

Figure 2:
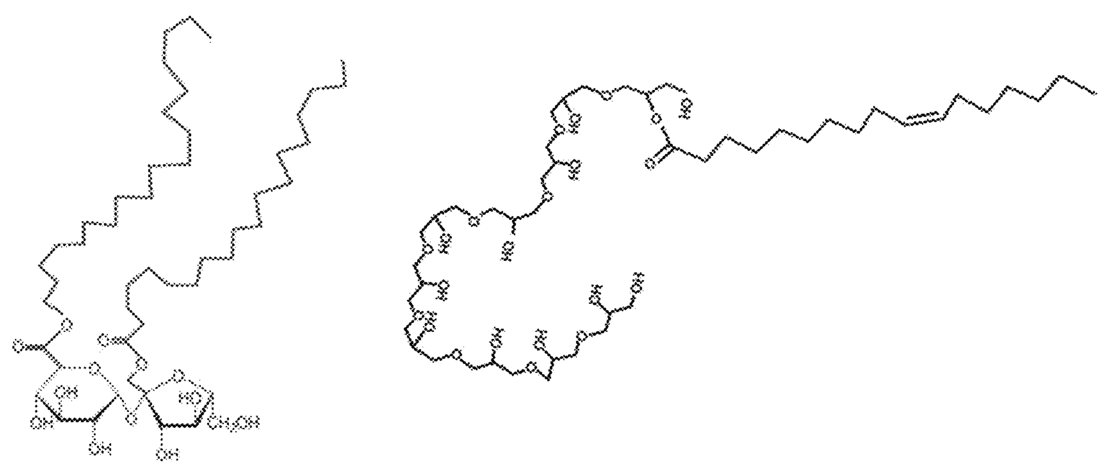
FIG. 2 illustrates a molecular structure of the mixed surfactant according to the present invention.

① Injecting surfactant
② Adjusting the pH to 9 to 11
③ Allowing reaction by stirring to increase purity
④ Adjusting the pH to 6 to 8
⑤ Cooling to 50° C. or lower to complete preparation FIG. 2 illustrates the molecular structures of sucrose distearate and polyglyceryl-10 oleate as surfactants. As can be seen from FIG. 2, stearic acid is bonded to the hydrophilic group of sucrose through two alkyl chains and one of the fatty acids of oleate is bonded to the hydrophilic group of polyglyceryl-10 through an ester bond.

These two surfactants may be a mixture of 5 to 40% by weight of sucrose distearate and 40 to 90% by weight of polyglyceryl-10 oleate. It should be noted that Example 2 is provided only as an example for better understanding, the present invention is not limited thereto and all of Examples 1 to 7 fall within the scope of the present invention.

Figure 3:
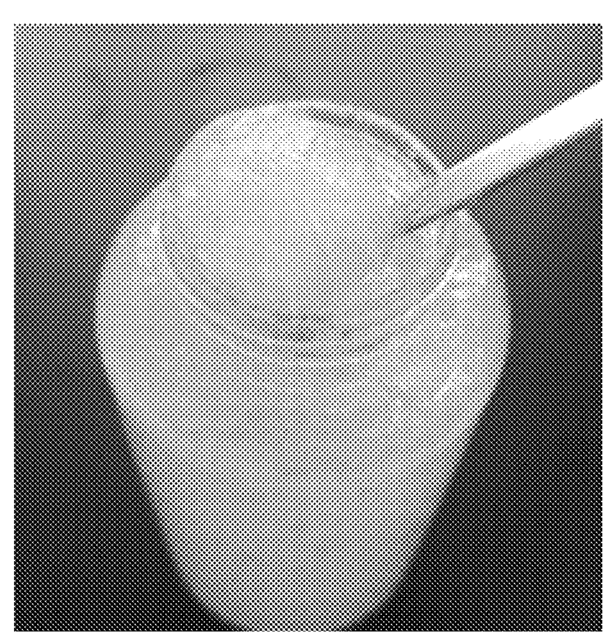
FIG. 3 is an image showing the prepared mixed surfactant of Example 2 of the present invention.

FIG. 3 is an image showing the high-purity mixed surfactant of the present invention (Example 2) which is capable of forming a transparent microemulsion without using a certain high-pressure microfluidizer. The high-purity mixed surfactant used herein is a light yellow paste with a unique odor, as shown in the image of FIG. 3. The high-purity mixed surfactant used herein has a specific gravity of 0.986, a pH of 6.9, an HLB of 11.8, and is highly soluble in oil and is soluble and dispersed well in polyol as well.

Preparation Example 1: Preparation of Mixed Surfactant

Figure 4:
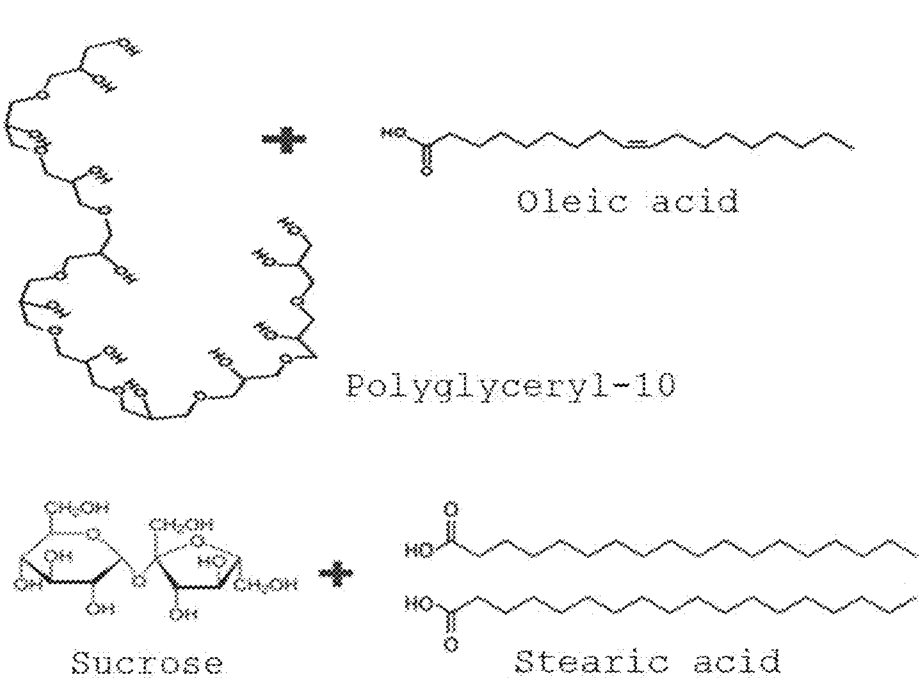
FIG. 4 illustrates a process of synthesizing sucrose distearate and polyglyceryl-10 oleate as components for the mixed surfactant of the present invention.

The process of synthetizing the mixed surfactant is shown in FIG. 4.

First, the molecular structures of sucrose and stearic acid for synthesis are shown. Sucrose was derived from sugarcane and stearic acid was derived from coconut. Two stearic acid fatty acids were esterified with sucrose to synthetize sucrose distearate.

Such a method includes mixing 342.3 g/mol of sucrose with 284.48 g/mol of stearic acid at a molar ratio of 1:2, dissolving the resulting mixture by heating to 120 to 180° C., adjusting a pH within 9 to 10.7, binding the fatty acids in the presence of nitrogen gas at 120 to 180° C. for 2 to 4 hours, adjusting the pH within 6 to 8 at 120 to 160° C., and cooling to 50° C. to complete preparation.

Meanwhile, a method for preparing polyglyceryl-10 oleic acid will be described as follows. The method includes mixing 758.8 g/mol of polyglyceryl-10 with 282.468 g/mol of oleic acid at a molar ratio of 1:1, dissolving the mixture by heating to 120 to 160° C., adjusting a pH within 9 to 10.7, binding the fatty acids in the presence of nitrogen gas at 120 to 160° C. for 2 to 4 hours, adjusting the pH within 6 to 8 at 120 to 160° C., and cooling to 50° C. to complete preparation.

The mixed surfactant is prepared by mixing 30% by weight of sucrose distearate prepared as above with 70% by weight of polyglyceryl-10 oleic acid prepared as above, adjusting the pH within 9 to 10.7, binding fatty acids in the presence of nitrogen gas at 120 to 160° C. for 2 to 4 hours, allowing the components to react while stirring to increase purity, adjusting the pH within 6 to 8 and cooling the reaction product to 50° C. or lower to complete preparation.

The high-purity mixed surfactant thus obtained was a light yellow paste with a unique odor, was dissolved when mixed with an oil and then heated, and had an HLB of 10.2 to 13.2. More specifically, polyglyceryl-10 oleate, which is one surfactant, has an HLB of 12.0 to 13.2 (average HLB=12.5), and sucrose distearate, which is the other surfactant, has an HLB of 4.5 to 6.9 (average HLB=6.3). When this surfactant is mixed with an oil, dissolved therein and then mixed with purified water, a transparent microemulsion can be formed by simple stirring.

In addition, the mixed surfactant is dissolved in glycerin, and an oil is added thereto, followed by stirring. When the phase transition temperature is reached to obtain a transparent nanoemulsion, the transparent nanoemulsion is stirred in the presence of prepared purified water to prepare a nanoemulsion having fine particles.

Examples 8 to 13: Preparation of Transparent Microemulsion Composition

The transparent microemulsion according to an embodiment of the present invention is prepared by mixing 12 to 25% by weight of the mixed surfactant obtained in Example 2 with 50 to 85% by weight of cetyl ethylhexanoate (oil phase) and 0.1 to 5% by weight of the mixed surfactant obtained in Example 2. As a representative example, when 20% by weight of the mixed surfactant, 78% by weight of cetyl ethylhexanoate (oil phase), and 2% by weight of purified water (aqueous phase) are mixed, a transparent microemulsion is formed by simple stirring.

The transparent microemulsion is a composition prepared by mixing the mixed surfactant of each of Examples 1 to 7 with cetyl ethylhexanoate (oil phase) and purified water, and may be used for skin toner, lotions, emulsions, essences, or creams to obtain any one of effects of facilitating percutaneous absorption, providing moisturizing activity, supplying nutrition, adjusting pH, controlling skin oil-moisture balance, alleviating fine wrinkles, and improving whitening and lifting activity.

Here, the oil phase may be oil such as cetyl ethylhexanoate, ethylhexyl palmitate, squalane, polydecene, capric/caprylic triglyceride, macadamia oil, apricot oil, argan oil, or camellia oil, but is not particularly limited thereto.

The method of preparing the cosmetic composition according to an embodiment of the present invention includes mixing a mixed surfactant with an oil, dissolving the mixed surfactant in the oil while heating at 68 to 85° C., and adding purified water to the result, followed by stirring at 700 to 4,000 rpm for 2 to 8 minutes to prepare a transparent microemulsion.

The technical feature of the present invention is that the transparent microemulsion can be prepared by simple stirring at 700 to 4,000 rpm without using a certain high-pressure microfluidizer.

It is important to mix the mixed surfactant prepared by mixing sucrose distearate with polyglyceryl-10 oleate, which are components according to an embodiment of the present invention, at a predetermined ratio so that a lamellar continuous structure can be stably formed. When a mixed system of the mixed surfactant with an oil reacts with purified water, it should be arranged linearly by hydrogen bonding and should have interfacial association to form a self-organized continuous structure.

Therefore, the combinations of mixed surfactants obtained according to the present invention can be easily arranged to form a continuous structure when mixed with various oils and to maintain thermodynamic stability.

Meanwhile, cetyl ethylhexanoate selected herein is an example of a non-polar oil with low polarity. The cetyl ethylhexanoate is selected because it can form a continuous lamellar structure well within the alkyl chain of the surfactant and thus is highly compatible with the mixed surfactant developed in the present invention.

Figure 5:
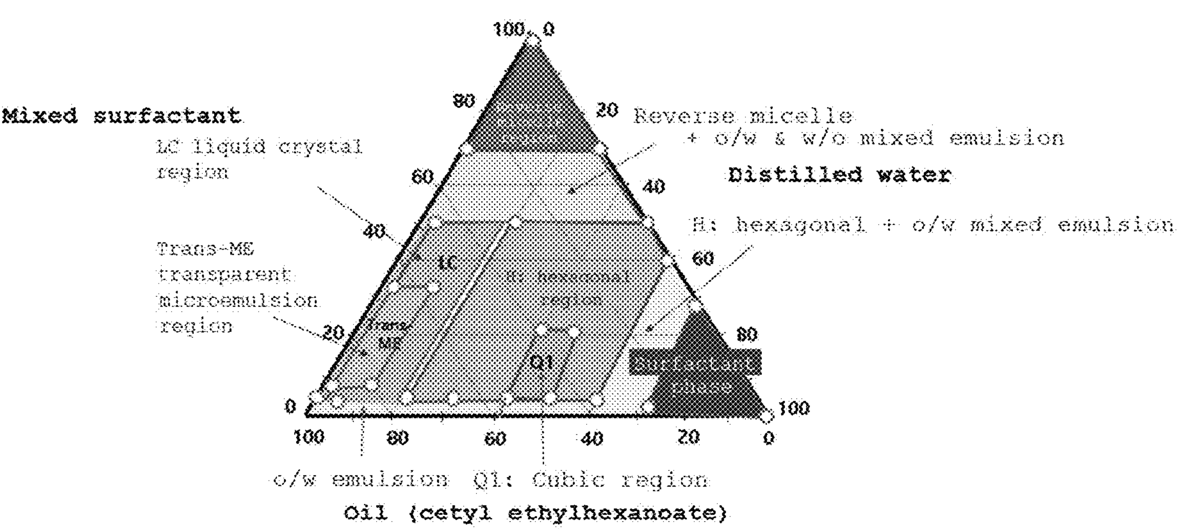
FIG. 5 is a component diagram illustrating regions where results are obtained in various forms in a ternary component system according to an embodiment of the present invention.

In the present invention, the region of the ternary component system where a transparent microemulsion is formed and other regions where interfacial chemical structures are formed are shown in FIG. 5.

As shown in FIG. 5, the transparent microemulsion has a structure in which hydrophilic and lipophilic groups are stacked in double layers horizontally and thus is called a "transparent microemulsion (Trans-ME)" in cosmetics. The transparent microemulsion has a configuration in which particles have a continuous lamella at the perimeter thereof. Based on this configuration, the transparent microemulsion can be formed even by simple stirring with a disper.

In addition, the lamellar crystal structure formed in the liquid crystal region (LC) is provided as a paste-like gel including micelles arranged in continuous multiple layers on a flat plate and such a flat lamellar gel structure is generally referred to as a "lamellar crystal (liquid crystal) structure". The cubic phase formed in the cubic region (Q1) has a square cubic structure. In addition, the hexagonal phase formed in the hexagonal region (H) has a hexagonal cylinder structure. Depending on the composition ratio of the ternary components, a variety of structures such as an oil-in-water O/W emulsion phase, a water-in-oil type W/O emulsion phase, a reverse micelle phase, a surfactant phase, a combination of a reverse micelle and a water-in-oil (W/O) emulsion phase, and a combination of a hexagonal phase and an O/W emulsion phase are formed.

Figure 6:
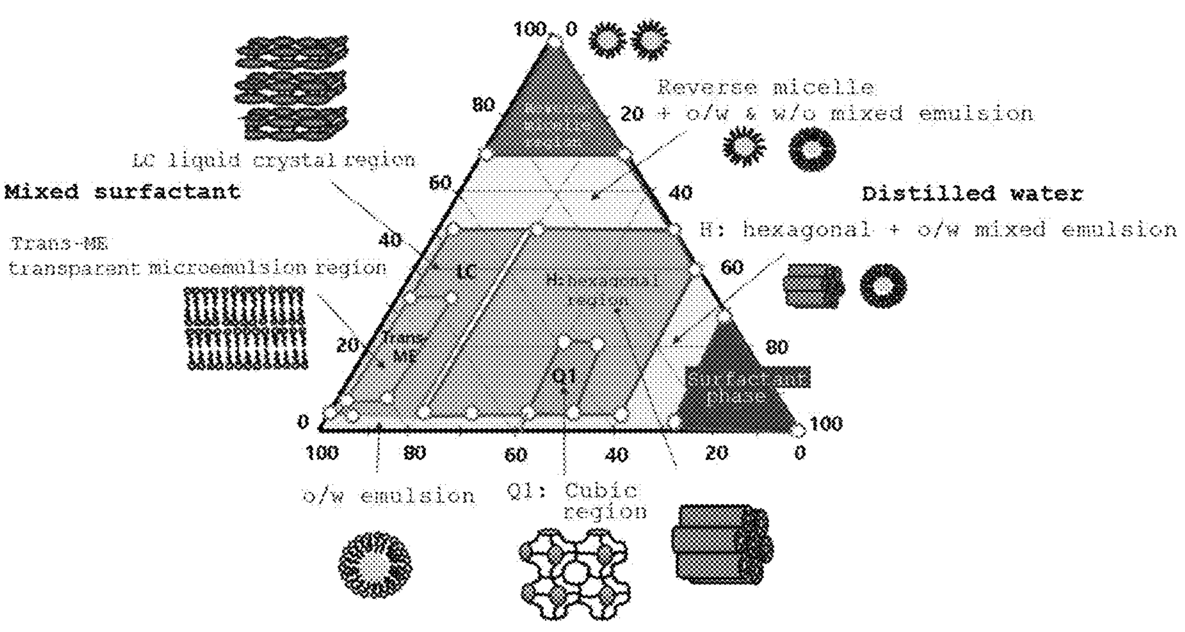
FIG. 6 is a component diagram illustrating structures of the results obtained in respective regions in a ternary component system according to an embodiment of the present invention.

FIG. 6 is a schematic diagram illustrating the structures formed in various regions depending on the mixing ratio of the mixed surfactant, the oil (cetyl ethylhexanoate), and purified water in the ternary component system. FIG. 6 schematically illustrates substances formed in the transparent microemulsion region (Trans-ME), the liquid crystal region (LC), the cubic region (Q1), the hexagonal region (H), the region of the reverse micelle+O/W and W/O combined emulsion, the region of hexagonal+O/W combined emulsion, the reverse micelle region, and the surfactant region.

Meanwhile, various conditions for preparing transparent microemulsions based on the mixed surfactant of Example 2 are shown in Examples 8 to 13 of Table 2. As can be seen from Examples 8 to 13, a transparent microemulsion is formed using 5 to 30% by weight of the mixed surfactant, 67.8 to 92.8% by weight of cetyl ethylhexanoate (oil phase), and 0.1 to 8% by weight of purified water (aqueous phase). The transparent microemulsion was a transparent liquid with a pH of about 6.12 to about 6.51. It can be seen that the specific gravity of the final product was in the range of 0.950 to 1.000. All the final products were stable after 4 weeks at 45° C.

TABLE 2

| | Examples 8 to 13 | | | | | |
|---|---|---|---|---|---|---|
| Component name | Example 8 (wt %) | Example 9 (wt %) | Example 10 (wt %) | Example 11 (wt %) | Example 12 (wt %) | Example 13 (wt %) |
| Example 2 (mixed surfactant) | 5 | 8 | 12 | 16 | 20 | 30 |
| Cetyl ethylhexanoate (oily phase) | 92.8 | 89.8 | 85.8 | 81.8 | 77.8 | 67.8 |
| Distilled water (aqueous phase) | 2 | 2 | 2 | 2 | 2 | 2 |
| Acetyl hexapeptide-8 (additive) | 0.1 | 0.1 | 0.1 | 0.1 | 0.1 | 0.1 |
| AHK-Cu peptide (additive) | 0.1 | 0.1 | 0.1 | 0.1 | 0.1 | 0.1 |
| Total | 100 | 100 | 100 | 100 | 100 | 100 |
| Appearance | Transparent liquid | Transparent liquid | Transparent liquid | Transparent liquid | Transparent liquid | Transparent liquid |
| pH (10% aqueous solution) | 6.32 | 6.46 | 6.28 | 6.12 | 6.46 | 6.51 |
| Specific gravity | 0.962 | 0.967 | 0.972 | 0.978 | 0.972 | 0.981 |
| Stability (after 4 weeks at 45° C.) | Stable | Stable | Stable | Stable | Stable | Stable |

[Preparation method]

1) A predetermined amount of the mixed surfactant of Example 2 and a predetermined amount of cetyl ethylhexanoate are heated to 80° C.

2) Distilled water (aqueous phase) and an additive are added thereto, followed by stirring at 50 to 68° C. and at 1,500 rpm for 5 minutes.

3) The reaction mixture is cooled to 30° C., followed by vacuum defoaming to complete preparation.

The additives in the composition in Table 2 above are substances that exhibit effects on the skin during the skin effect test on the formulation of the present invention. Therefore, these additives are components that do not affect the preparation of the microemulsion or nanoemulsion structure of the present invention.

Figure 7:
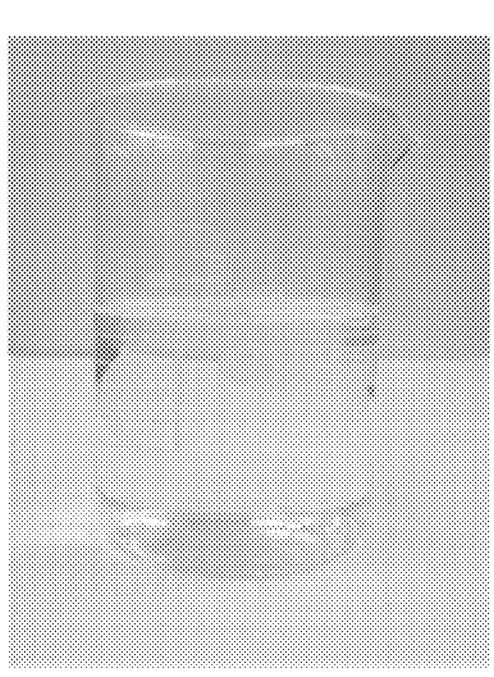
FIG. 7 is an image showing a transparent microemulsion according to an embodiment of the present invention.

Meanwhile, FIG. 7 is an image showing a transparent microemulsion formed in the ternary component system shown in Example 2. For the ternary components in FIG. 6, the mixed surfactant of Example 2 was used as the surfactant, the cetyl ethylhexanoate was used as the oil, and the purified water was used, and the mixed surfactant of Example 2 was used in an amount of 20% by weight, the cetyl ethylhexanoate was used in an amount of 78% by weight, and the purified water was used in an amount of 2% by weight. As a result, a stable and transparent microemulsion was formed.

Figure 8:
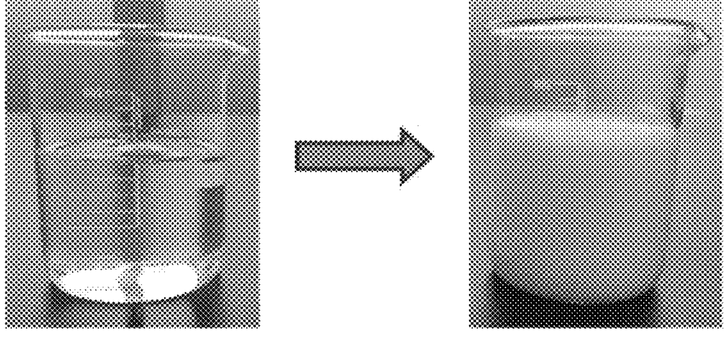
FIG. 8 is an image showing an emulsion obtained by diluting the result of FIG. 6 in purified water.

Meanwhile, FIG. 8 illustrates a transparent microemulsion (left image) obtained in an embodiment of the present invention. When 10 g of a transparent microemulsion is mixed with 90 g of water, followed by stirring with a disper (at 100 to 700 rpm), it is phase-changed into a milky white O/W emulsion (right image). This is especially suited to development of cleansing cosmetics or mask sheet formulations.

Figure 9:
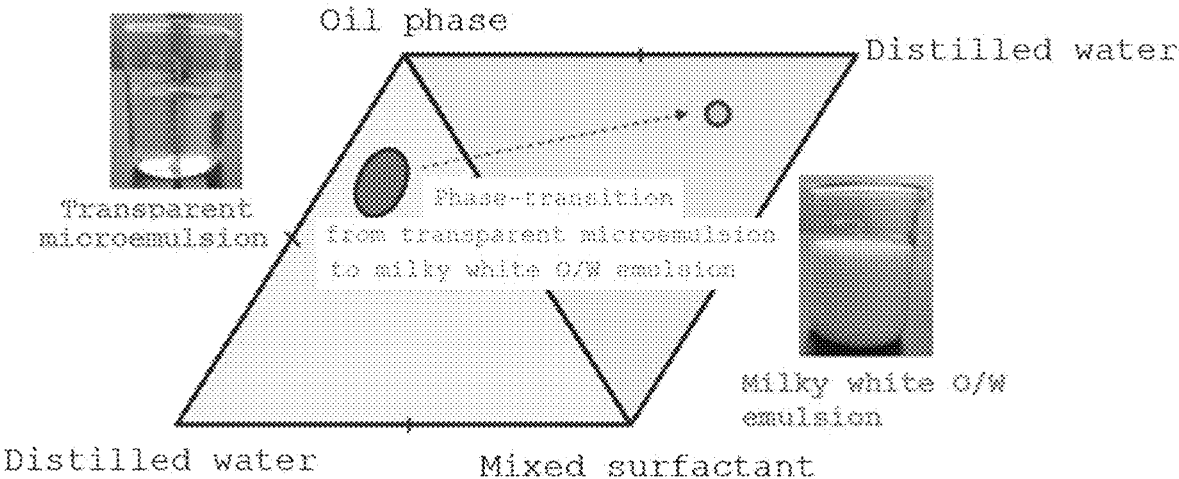
FIG. 9 illustrates a transparent microemulsion formation region in a ternary component system according to an embodiment of the present invention and a white emulsion formed by mixing the transparent microemulsion with purified water.

FIG. 9 is a schematic diagram illustrating the phenomenon in which a transparent microemulsion undergoes phase transition to milky white. FIG. 9 illustrates the phenomenon in which, when a transparent microemulsion is diluted in purified water, followed by stirring, it undergoes phase-transition to a milky white O/W emulsion. Using this phenomenon, the oiliness of skin texture can be controlled. The transparent microemulsion can be easily used depending on the skin type or age. In other words, an appropriate amount of transparent microemulsion may be diluted in water to prepare an O/W emulsion-type gel cream, and the transparent microemulsion may be utilized in a variety of applications such as ampoule essences, mask sheets, and cleansing tissues, even without using a certain heating process. This is one of the technical features of the present invention. In this regard, the present invention may be an energy-saving or carbon-reducing eco-friendly technology.

Examples 14 to 18: Preparation of Fine Nanoemulsion

In this example, a fine nanoemulsion was prepared using the mixed surfactant of the present invention with the composition shown in Table 3 below. The present example is a method of preparing a fine nanoemulsion. A lotion or ampoule essence prepared from the fine nanoemulsion has advantages of appearance suitable for blue light depending on the particle size, excellent skin absorption, and superior texture.

TABLE 3

| | | Examples 14 to 18 | | | | |
|---|---|---|---|---|---|---|
| Phase | Component name | Example 14 (wt %) | Example 15 (wt %) | Example 16 (wt %) | Example 17 (wt %) | Example 18 (wt %) |
| A | Example 2 (mixed surfactant) | 3 | 6 | 7 | 10 | 11 |
| B | Glycerin | 5 | 6 | 7 | 8 | 8 |
| | Distilled water | 3 | 10 | 15 | 15 | 20 |
| C | Cetyl ethylhexanoate | 5 | 10 | 15 | 20 | 30 |
| D | GHK-Cu peptide | 0.1 | 0.1 | 0.1 | 0.1 | 0.1 |
| | Acetyl hexapeptide | 0.1 | 0.1 | 0.1 | 0.1 | 0.1 |
| | Distilled water (aqueous phase) | 83.8 | 67.8 | 55.8 | 46.8 | 30.8 |
| Total | | 100 | 100 | 100 | 100 | 100 |
| Appearance | | Nanoemulsion | Nanoemulsion | Nanoemulsion | Nanoemulsion | Nanoemulsion |
| Phase | | Liquid | Liquid | Liquid | Liquid | Liquid |
| pH | | 6.2 | 6.3 | 6.5 | 6.6 | 6.5 |
| Average particle size (nm) | | 59.56 | 73.82 | 123.63 | 168.87 | 237.27 |
| Specific gravity | | 1.02 | 1.06 | 1.09 | 1.06 | 1.07 |
| Stability (after 4 weeks at 45° C.) | | Stable | Stable | Stable | Stable | Stable |

[Preparation method]

1) A predetermined amount of the mixed surfactant (Phase A) of the Example 2 is dissolved in predetermined amounts of glycerin and distilled water (Phase B) by cooling to 70° C.

2) Cetyl ethylhexanoate (oily phase; Phase C) is added to the result, followed by stirring to prepare Phase D gel. A solution of an additive in distilled water (Phase D) is added to the gel, followed by stirring (at 1,600 rpm for 5 minutes).

3) The result is cooled to 30° C., followed by vacuum deforming to obtain a final product called "fine nanoemulsion".

Figure 10:
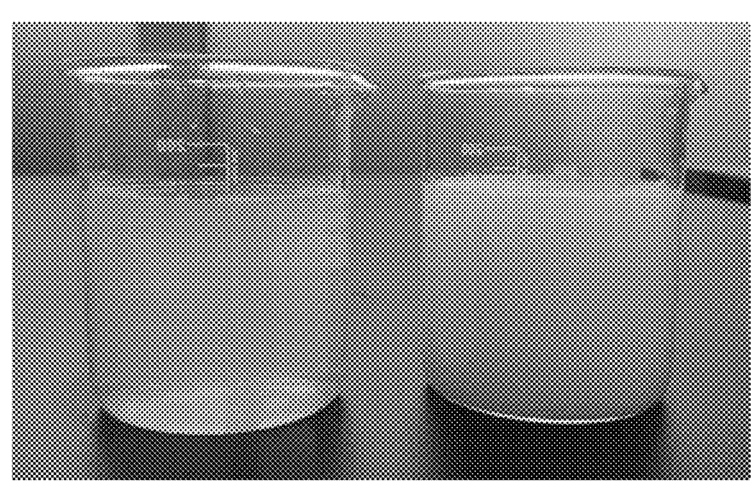
FIG. 10 is an image showing the formation of a fine nanoemulsion according to an embodiment of the present invention.

FIG. 10 is an image showing the fine nanoemulsion obtained in the present example. The image on the left shows the product of Example 14 which was a fine nanoemulsion with a particle size of about 59.56 nm. The fine nanoemulsion appears as a translucent emulsion. The image on the right of FIG. 10 shows the product of Example 17, which was a stable emulsion without causing phase separation although it has a particle size of about 168.87 nm.

As described above, a fine nanoemulsion can be prepared from the mixed surfactant prepared in the present invention without using a special high-pressure microfluidizer. In particular, it is a remarkable feature of the present invention that the preparation of a fine nanoemulsion with the characteristics was completed using a surfactant composition containing no polyethylene glycol (PEG). In particular, the innovative feature of the present invention is to use a mixed surfactant of the sucrose distearate and polyglyceryl-10 oleate.

The emulsion using 3 to 11% by weight of polysorbate 60 as a conventional surfactant and 5 to 30% by weight of an oil phase is usually milky white and has a particle size of about 8.560 μm. In addition, when a liposome emulsion containing 3 to 11% by weight of hydrogenated lecithin, which forms conventional liposomes, and 5 to 30% by weight of the oil phase was allowed to pass through a high pressure microfluidizer (10,000 psi, 50° C., 3 times), a milky white emulsion with a particle size of 826.72 nm was obtained. On the other hand, in Example 19 of the present invention, fine nanoparticles with a size of 72.95 nm were formed, which is a feature distinctive from the prior art. This particle size may be much smaller when taking into consideration the fact that liposomes, which are usually formed by passing through a microfluidizer 2 to 6 times, have a size of 200 to 950 nm.

Figure 11:
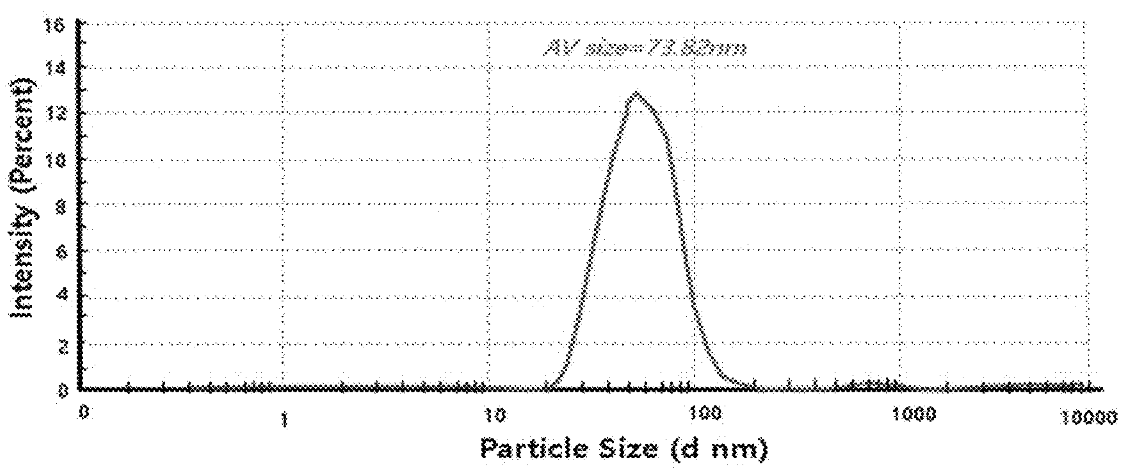
FIG. 11 is an image showing the particle size of emulsified particles of the fine nanoemulsion prepared according to an embodiment of the present invention.

FIG. 11 is a particle size distribution of the emulsion of Example 15 using a particle size meter, Zeta Sizer-PTX (UK). As can be seen from the result, the particle size falls within a range from 5 nm to 125 nm, and the average particle diameter is 73.82 nm, indicating that the emulsion has a fine particle size. Further, it was confirmed that the emulsion had a uniform particle size distribution. Based on these characteristics, it is expected that the emulsion can be absorbed quickly into the skin, resulting in excellent oil-moisture balance control and moisturizing improvement effects.

Experimental Example 1: Skin Efficacy Test of Examples of the Present Invention

In this experiment, samples were prepared and skin efficacy was tested as shown in Table 4 below.

TABLE 4

Example 19, Comparative Example 1 and Comparative Example 2

| Component name | Comparative Example 1 (wt %) O/W emulsion | Comparative Example 2 (wt %) General liposome | Example 19 (wt %) Fine nanoemulsion |
|---|---|---|---|
| 1. Polysorbate 60 | 10 | — | — |
| 2. Hydrogenated lecithin | — | 10 | — |
| 3. Example 2 (mixed surfactant) | — | — | 10 |
| 4. Cetyl ethylhexanoate (oily phase) | 20 | 20 | 20 |
| 5. Distilled water (aqueous phase) | 62.9 | 62.9 | 62.9 |
| 6. Glycerin (aqueous phase) | 7 | 7 | 7 |
| 7. AHK-Cu peptide (additive) | 0.1 | 0.1 | 0.1 |
| Total | 100 | 100 | 100 |
| Appearance | Milky lotion | Milky lotion | Translucent lotion |
| pH | 6.22 | 6.31 | 6.28 |
| Average particle size (nm) | 8,560 | 826.72 | 72.95 |
| Specific gravity | 1.05 | 1.03 | 1.02 |

[Preparation method]
1) Components 1 to 3 are weighed and component 4 is added to components 1 to 3, followed by dissolution while heating to 78 to 90° C.
2) Components 5 and 6 are added thereto, followed by stirring at 78 to 80° C. at 4,500 rpm for 5 minutes.
3) The result is cooled to 30° C., followed by vacuum defoaming to complete preparation.

Skin absorption, skin moisturizing, and fine wrinkle alleviation effects of Comparative Examples 1 and 2 and Example 19 (Fine nanoemulsion) were tested. Comparative Example 1 is a general O/W emulsion and Comparative Example 2 is a general liposome. Example 19 is a fine nanoemulsion of the present invention. The effects of the present invention could be confirmed by comparison therebetween.

1. Percutaneous Absorption

Percutaneous absorption of Comparative Examples 1 and 2, and Example 19 (fine nanoemulsion) was measured.

Percutaneous absorption was tested by tape stripping using AHK-Cu peptide as an indicator. The sample for testing percutaneous absorption contains 1,000 ppm of AHK-Cu peptide as in Example 19. The test method is as follows. A square with a width of 1 cm and a length of 1 cm was drawn on the lower forearm and 0.1 mg of the sample was applied thereto twice every 5 minutes. After 8 hours, an exfoliation tape was stripped in the applied area 9 times, stored separately, was further stripped therein 10 to 15 times and quantitatively analyzed by HPLC.

Figure 12:
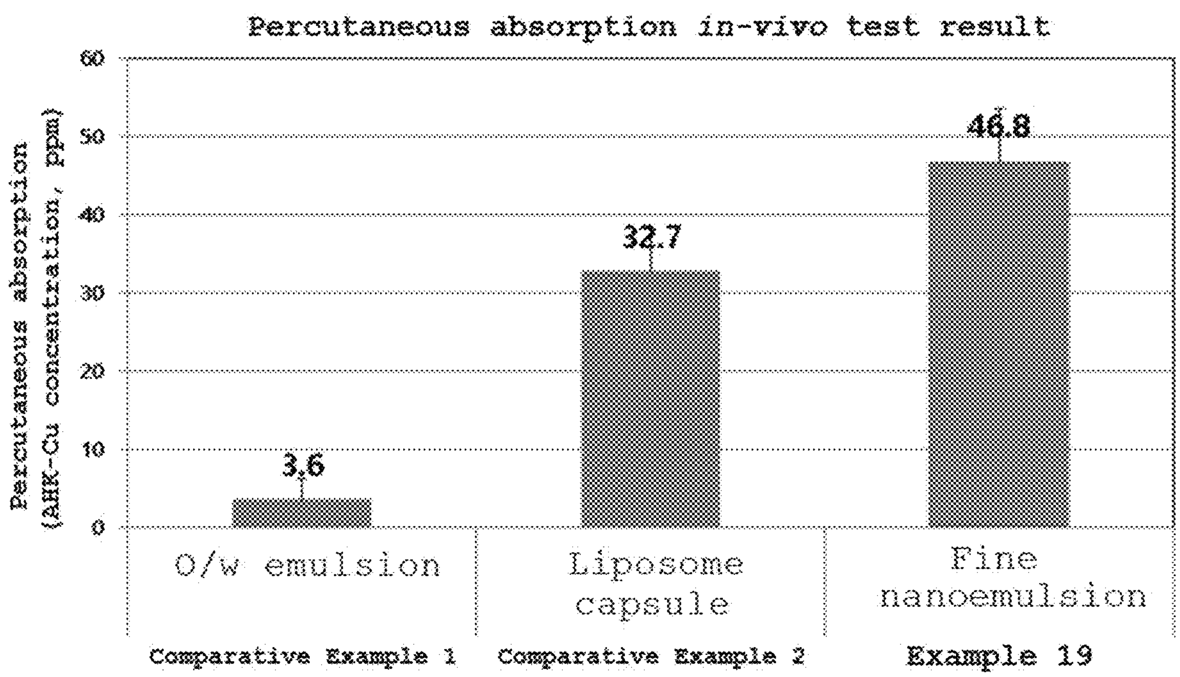
FIG. 12 is a graph showing the percutaneous absorption effect of the fine nanoemulsion according to an embodiment of the present invention.

The results are shown in the graph of FIG. 12. The samples stripped 1 to 9 times were excluded from the results of the present invention because the amounts of the samples correspond to the amount of adenosine in the epidermal layer. Quantitative analysis was conducted on 6 subjects (in their 20s to 60s, male and female), the number of measurements was 3 times and the average of the measured values was obtained. The amounts of AHK-Cu peptides detected in Example 19 along with Comparative Examples 1 and 2 are shown. 3.6 ppm of AHK-Cu peptide was detected in Comparative Example 1 (O/W emulsion), 32.7 ppm of AHK-Cu peptide was detected in Comparative Example 2 (general liposome), and 46.8 ppm of AHK-Cu peptide was detected in Example 19.

It was found that the fine nanoemulsion of Example 19 had at least 14.6 times higher percutaneous absorption than Comparative Example 1 and at least 1.43 times higher than Comparative Example 2. These results showed that Example 19 exhibited much better percutaneous absorption than Comparative Examples 1 and 2. The reason for this is that the fine nanoemulsion of the present invention has a much finer particle size than both of Comparative Examples and is absorbed in a higher amount quickly. In addition, another reason is that a fine nanoemulsion can be prepared without passage through a high-pressure microfluidizer.

2. Evaluation of Skin Moisturizing Effect

The skin moisturizing effect of Comparative Examples 1 and 2, and Example 19 (fine nanoemulsion) was measured.

The moisturizing effect test was conducted on 6 subjects (in their 20s to 60s, male and female), measurement was performed 3 times and the average of the measured values was obtained. A predetermined amount (2 g) of each sample was applied to the face twice a day (morning and evening) over 4 weeks and the moisture content of a specific spot of the skin was measured using a moisture meter in an incubator unaffected by humidity. The results of measurement only after 4 weeks are shown.

Figure 13:
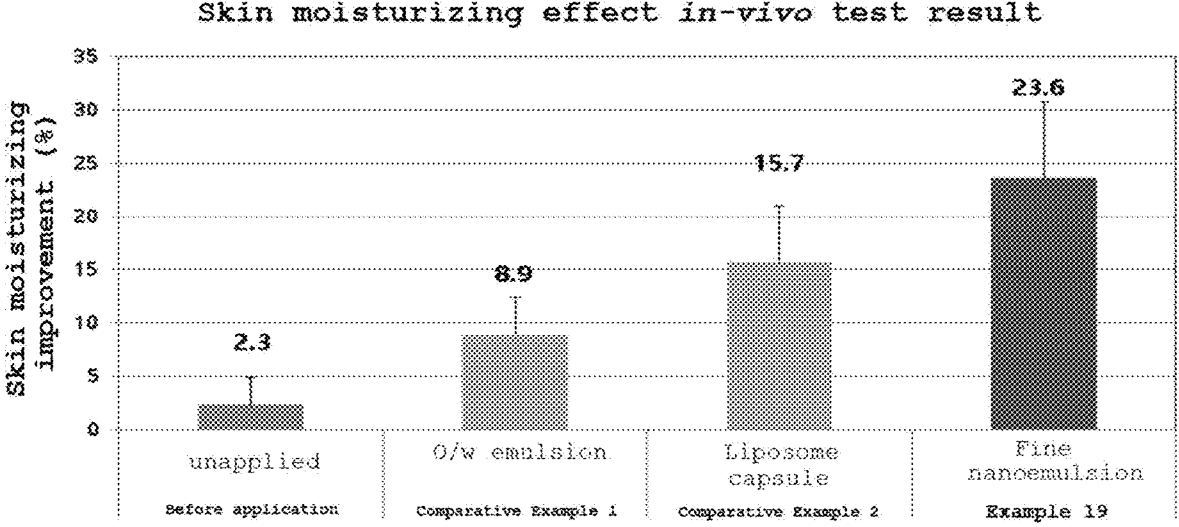
FIG. 13 is a graph showing the moisturizing effect of the fine nanoemulsion according to an embodiment of the present invention.

The results are shown in FIG. 13. The skin moisture content before application was 2.3%. Four weeks after application, the skin moisture content was 8.9%, 15.7%, and 23.6% for Comparative Example 1, Comparative Example 2, and Example 1, respectively. It can be seen that the moisture content of Example 19 was significantly increased compared to those of Comparative Examples 1 and 2.

3. Fine Wrinkle Alleviation Effect

The fine wrinkle alleviation effect of the fine nanoemulsion of the present invention based on fast percutaneous absorption was clinically tested. The effect of alleviating skin fine wrinkles of Example 19 and Comparative Examples 1 and 2 was tested.

The test was performed using a skin wrinkle meter from Aramo TS (Korea). A predetermined amount (2 g) of each sample was applied to the entire face twice a day (morning and evening) over 4 weeks, and the alleviation of skin fine wrinkles was measured numerically in the certain spot around the eyes (around the eyebrows, where fine wrinkles are most common) after 4 weeks. The skin fine wrinkles were measured three times on 12 subjects for each sample and a final score was determined using the average of the three measured values.

Figure 14:
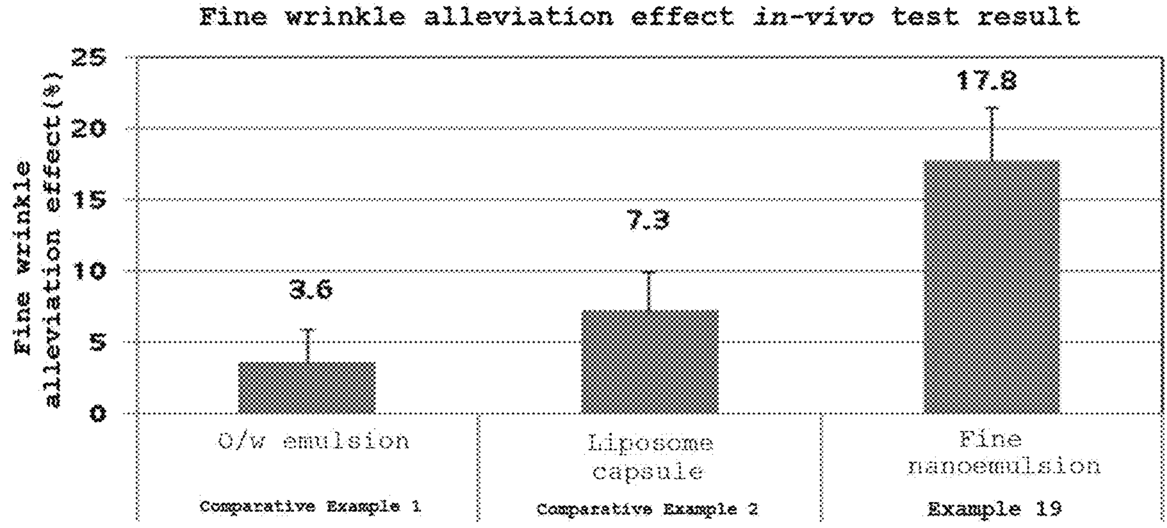
FIG. 14 is a graph showing the fine wrinkle alleviation effect of the fine nanoemulsion according to an embodiment of the present invention.

The results of measurement of the effect of alleviating fine wrinkles around the eyes are shown in FIG. 14. Comparative Example 1 exhibited a fine wrinkle alleviation of 3.6%, Comparative Example 2 exhibited a fine wrinkle alleviation of 7.3%, and Example 19 exhibited a fine wrinkle alleviation of 17.8%. This result shows that Example 19 has at least 4.9 times higher fine wrinkle alleviation effect than Comparative Example 1 and at least 2.4 times higher fine wrinkle alleviation effect than Comparative Example 2. This results from the fact that the AHK-Cu peptide is finely nanoemulsified and is thus percutaneously absorbed faster and better than other Comparative Examples.

4. Whitening Effect

2% of niacinamide as a generally known whitening component was added to the fine nanoemulsion of the present invention to prepare a fine nanoemulsion of Example 20 and then whitening effect thereof was measured.

The fine nanoemulsion (Example 20), a general O/W emulsion (Comparative Example 3), and a general liposome (Comparative Example 4) contained the same concentration of whitening component and the whitening performance was tested in-vivo clinically under the same conditions (Table 5).

TABLE 5

Example 20, Comparative Example 3 and Comparative Example 4

| Component name | Comparative Example 3 (wt %) O/W emulsion | Comparative Example 4 (wt %) General liposome | Example 20 (wt %) Fine nano emulsion |
|---|---|---|---|
| 1. Polysorbate 60 | 10 | — | — |
| 2. Hydrogenated lecithin | — | 10 | — |
| 3. Example 2 (mixed surfactant) | — | — | 10 |
| 4. Cetyl ethylhexanoate (oily phase) | 20 | 20 | 20 |
| 5. Distilled water (aqueous phase) | 61 | 61 | 61 |
| 6. Glycerin (aqueous phase) | 7 | 7 | 7 |
| 7. Niacinamide (additive) | 2 | 2 | 2 |
| Total | 100 | 100 | 100 |
| Appearance | Milky lotion | Milky lotion | Translucent lotion |
| pH | 6.22 | 6.31 | 6.28 |
| Average particle size (nm) | 8,710 | 878.55 | 70.26 |
| Specific gravity | 1.02 | 1.01 | 1.05 |

[Preparation method]
1) Components 1 to 3 are weighed and component 4 is added to components 1 to 3, followed by dissolution while heating to 78 to 90° C.
2) Components 5 and 6 are added thereto, followed by stirring at 78 to 80° C. at 4,500 rpm for 5 minutes.
3) The result is cooled to 30° C., followed by vacuum defoaming to complete preparation.

The test was performed using a measuring device from Aramo TS (Korea) quantifying the degree to which the skin is clear and calculating the reduction effect of melanin deposited on the skin. In-vivo clinical evaluation was performed as follows. A predetermined amount of each sample was applied to the entire face twice a day (morning and evening) over 4 weeks, and the skin whitening effect was quantified in the certain spot areas on the face after 4 weeks. The skin whitening effect was measured three times on 12 subjects for each sample and a final score was determined using the average of the three measured values.

Figure 15:
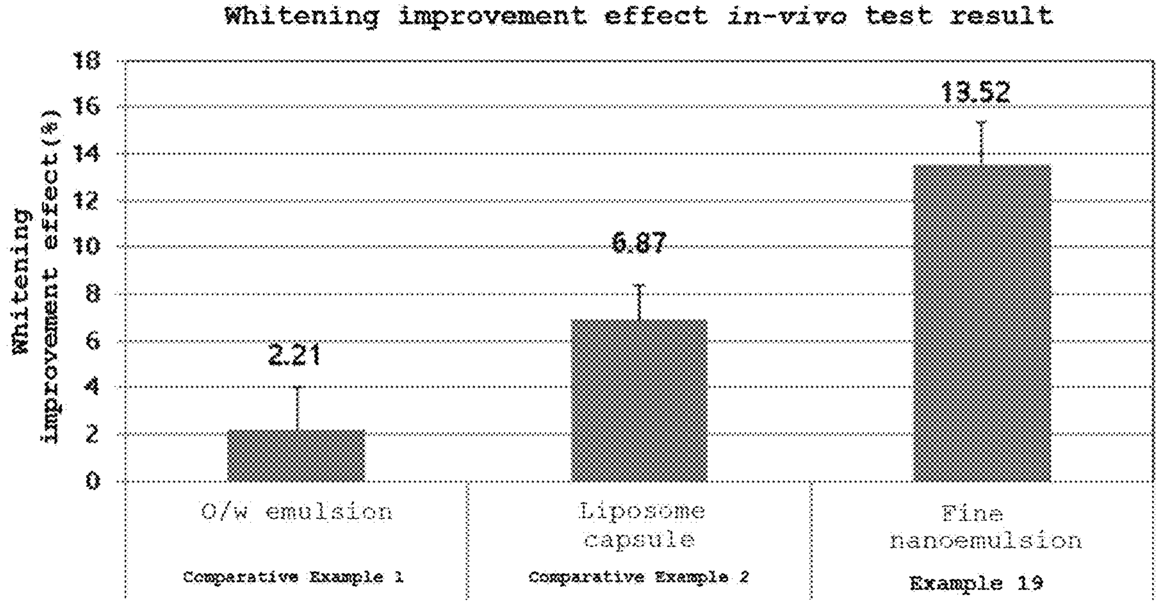
FIG. 15 is a graph showing the whitening improvement effect of the fine nanoemulsion according to an embodiment of the present invention.

The results of measurement are shown in FIG. 15. Comparative Example 1 exhibited a skin whitening improvement of 2.21%, Comparative Example 2 exhibited a skin whitening improvement of 6.87%, and Example 20 exhibited a skin whitening improvement of 13.52%, meaning clear skin. This result shows that Example 20 has at least 6.1 times considerably higher skin whitening improvement effect than Comparative Example 3 and at least 1.96 times considerably higher skin whitening improvement effect than Comparative Example 4.

4. Skin Lifting Improvement

An in-vivo experiment to improve skin lifting effect was performed using Example 19 and Comparative Examples 1 and 2.

The test was performed using a skin lifting meter from Aramo TS (Korea). Skin lifting evaluation was performed as follows. A predetermined amount of each sample was applied to the entire face twice a day (morning and evening) over 4 weeks, and the skin lifting effect after 4 weeks was measured in the certain area on the face. The skin lifting effect was measured three times on 10 subjects for each sample and a final score was determined using the average of the three measured values.

Figure 16:
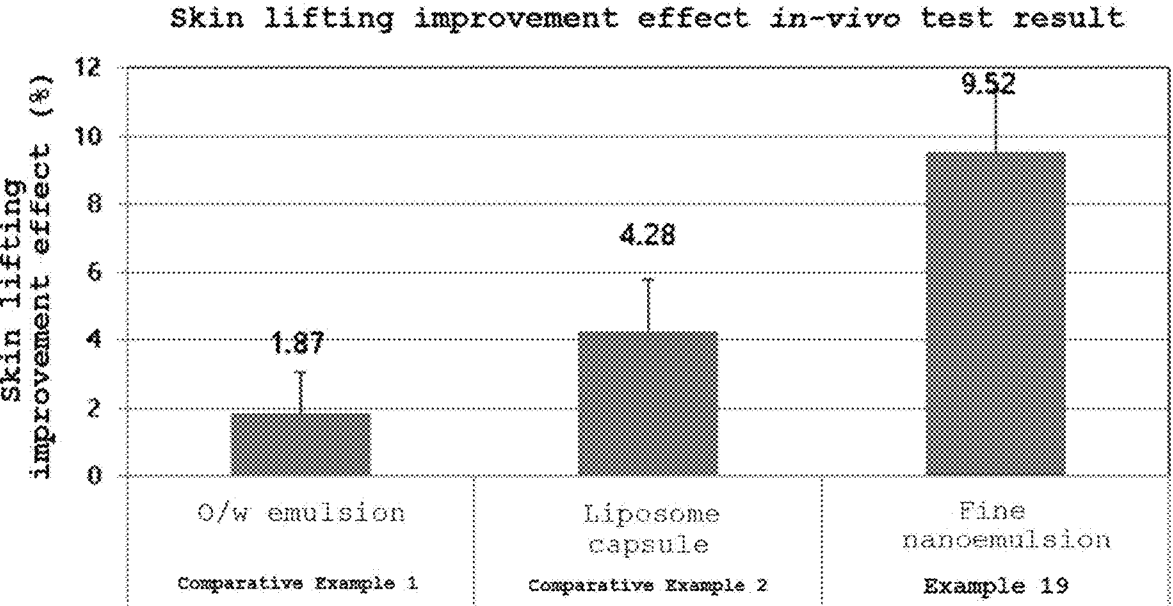
FIG. 16 is a graph showing the skin lifting improvement effect of the fine nanoemulsion according to an embodiment of the present invention.

The results of lifting measurement are shown in FIG. 16. Comparative Example 1 exhibited a skin lifting improvement of 1.87%, Comparative Example 2 exhibited a skin lifting improvement of 4.28%, and Example 19 exhibited a skin lifting improvement of 9.52%. This result shows that Example 19 has at least 5 times higher skin lifting improvement effect than Comparative Example 1 and at least 2.2 times higher skin lifting improvement effect than Comparative Example 2.

5. Skin pH Improvement Effect

A skin pH improvement effect of Example 19, Example 20, and Comparative Examples 1 and 2 was tested.

The test was performed using a skin pH meter from Aramo TS (Korea). Skin lifting test was performed as follows. A predetermined amount of each sample was applied to the entire face twice a day (morning and evening) over 4 weeks, and the pH was measured on the face after 4 weeks. The skin pH was measured three times on 10 subjects for each sample and a final score was determined using the average of the three measured values.

The results of measurement are shown in FIG. 17. Comparative Example 1 exhibited a pH of 6.12, Comparative Example 2 exhibited a pH of 5.85, and Example 19 exhibited a pH of 5.53. The result showed pH was shifted to an acidic range lower than 6.18, the average pH before use. These results show that the pH of Example 19 or Example 20 shifts to a more acidic range than Comparative Examples 1 and 2.

As described above, the microemulsion according to present invention is quickly absorbed into the skin, and exhibits excellent skin improvement effects such as moisturizing, fine wrinkle alleviation, whitening and lifting improvement and pH improvement.

Formulation Example 1: Preparation of Various Cosmetic Formulations Using the Present Invention It would be obvious that various modifications, additions and substitutions are possible, without departing from the scope and spirit of the invention as disclosed in the accompanying claims. Therefore, the scope of the present invention is not limited by the examples described above and is defined only by the claims and equivalents thereto.

Several types of cosmetic compositions according to examples will be illustrated and the present invention is not limited thereto.

TABLE 6

| Cleansing oil | | | | |
|---|---|---|---|---|
| Component name | | Example 21 (wt %) | Example 22 (wt %) | Example 23 (wt %) |
| Phase A | Example 2 (mixed surfactant) | 15 | 20 | 25 |
| Phase B | Cetyl ethylhexanoate | 30 | 25 | 20 |
| | Ethylhexyl palmitate | 20 | 15 | 18 |
| | Jojoba oil | 10 | 12 | 10 |
| | Apricot oil | 8 | 10 | 12 |
| | Capric/caprylic triglyceride | 6.85 | 6.95 | 6.95 |
| | Argan tree oil | 5 | 5.9 | 2.9 |
| | Tocopheryl acetate | 0.1 | 0.1 | 0.1 |
| | Ascorbyl tetraisopalmitate | 3 | 3 | 3 |
| | Lavender oil | 0.05 | 0.05 | 0.05 |
| Phase C | Distilled water | 1.7 | 1.7 | 1.7 |
| | Purslane extract | 0.1 | 0.1 | 0.1 |
| | Green tea extract | 0.1 | 0.1 | 0.1 |
| | Cucumber extract | 0.1 | 0.1 | 0.1 |
| Total | | 100 | 100 | 100 |
| Appearance | | Transparent Liquid | Transparent liquid | Transparent liquid |
| pH | | 5.73 | 5.81 | 5.85 |
| Odor | | Lavender scent | Lavender scent | Lavender scent |
| Specific gravity | | 1.002 | 1.003 | 1.005 |
| Stability (45° C., 3 months) | | Stable | Stable | Stable |

[Preparation method]

1) Phase A and Phase B are weighed, followed by dissolution while heating to 75 to 80° C.

2) Phase C is stirred along with the result at 120 to 500 rpm for 5 minutes.

3) When a transparent microemulsion is obtained, it is further stirred at 120 to 500 rpm for 5 minutes.

4) The result is cooled to 30° C., followed by vacuum defoaming to complete preparation.

TABLE 7

| Skin toner | | | | |
|---|---|---|---|---|
| Component name | | Example 24 (wt %) | Example 25 (wt %) | Example 26 (wt %) |
| Phase A | Example 2 (mixed surfactant) | 3 | 5 | 7 |
| | Cetyl ethylhexanoate | 1 | 2 | 3 |
| | Green tea oil | 0.5 | 0.6 | 1 |
| | Cottonseed oil | 0.3 | 0.4 | 0.5 |
| | Rapeseed oil | 0.2 | 0.2 | 0.2 |
| | Tocopheryl acetate | 0.1 | 0.1 | 0.1 |
| | Camellia oil | 0.1 | 0.1 | 0.1 |
| Phase B | Glycerin | 3 | 4 | 5 |
| | Distilled water | 2 | 3 | 5 |
| Phase C | 1,3-butylene glycol | 5 | 5 | 5 |
| | 1,2-hexanediol | 2 | 2 | 2 |
| | EDTA-2Na | 0.03 | 0.03 | 0.03 |
| | Allantoin | 0.01 | 0.01 | 0.01 |
| | Ethyl ascorbic acid | 0.2 | 0.2 | 0.2 |
| | Acetyl hexapeptide-8 | 0.05 | 0.05 | 0.05 |
| | Distilled water | 81.88 | 76.68 | 70.18 |
| | Peppermint oil | 0.03 | 0.03 | 0.03 |
| | Polyglyceryl-10 stearate/polyglyceryl-10 oleate | 0.3 | 0.3 | 0.3 |
| Phase D | Sodium hyaluronate | 0.1 | 0.1 | 0.1 |
| | Idebenone | 0.1 | 0.1 | 0.1 |
| | Red ginseng extract | 0.1 | 0.1 | 0.1 |
| Total | | 100 | 100 | 100 |
| Appearance | | Translucent liquid | Translucent liquid | Translucent liquid |
| pH | | 5.36 | 5.62 | 5.78 |
| Average particle size (nm) | | 68.25 | 95.22 | 128.51 |
| Specific gravity | | 1.001 | 1.005 | 1.008 |
| Stability (45° C., 3 months) | | Stable | Stable | Stable |

[Preparation method]

1) Phase A is weighed and dissolved while heating to 85 to 95° C.

2) The result is mixed with Phase B, followed by stirring with a disper while slowly cooling from 90° C. to 55° C.

3) When the result is converted into a transparent phase at about 65 to about 58° C., Phase C is added thereto, followed by stirring to obtain a nanoemulsion.

4) Phase D is added to the nanoemulsion, followed by stirring.

5) The result is cooled to 30° C., followed by vacuum defoaming to complete preparation.

TABLE 8

| Lotion emulsion | | | | |
|---|---|---|---|---|
| Component name | | Example 27 (wt %) | Example 28 (wt %) | Example 29 (wt %) |
| Phase A | Example 2 (mixed surfactant) | 5 | 7 | 10 |
| | Cetyl ethylhexanoate | 5 | 5 | 7 |
| | Macadamia oil | 0.8 | 0.6 | 1 |
| | Argan oil | 0.6 | 0.4 | 0.5 |
| | Olive oil | 0.5 | 0.2 | 0.2 |
| | Tocopheryl acetate | 0.1 | 0.1 | 0.1 |
| | Camellia oil | 0.5 | 0.1 | 0.1 |
| Phase B | Glycerin | 5 | 7 | 10 |
| | Distilled water | 6 | 7 | 8 |
| Phase C | 1,3-butylene glycol | 6 | 8 | 10 |
| | 1,2-hexanediol | 2 | 2 | 2 |
| | EDTA-2Na | 0.05 | 0.05 | 0.05 |
| | Allantoin | 0.01 | 0.01 | 0.01 |
| | Ethyl ascorbic acid | 0.2 | 0.2 | 0.2 |
| | Turmeric root extract | 0.1 | 0.1 | 0.1 |
| | Distilled water | 67.04 | 61.14 | 49.64 |
| | Lavender citrus fragrance | 0.05 | 0.05 | 0.05 |
| | Polyglyceryl-10 stearate/polyglycery 1-10 oleate | 0.3 | 0.3 | 0.3 |
| | Carbomer-941 | 0.35 | 0.35 | 0.35 |
| | Transparent xanthan gum | 0.1 | 0.1 | 0.1 |
| Phase D | Purslane extract | 0.1 | 0.1 | 0.1 |
| | Pomegranate extract | 0.1 | 0.1 | 0.1 |
| | Pine mushroom extract | 0.1 | 0.1 | 0.1 |
| Total | | 100 | 100 | 100 |
| Appearance | | low-viscosity fluid | low-viscosity fluid | low-viscosity fluid |

TABLE 8-continued

| Lotion emulsion | | | |
|---|---|---|---|
| Component name | Example 27 (wt %) | Example 28 (wt %) | Example 29 (wt %) |
| pH | 5.72 | 5.68 | 5.83 |
| Average particle size (nm) | 125.61 | 187.32 | 210.55 |
| Specific gravity | 0.998 | 0.999 | 0.996 |
| Stability (45° C., 3 months) | Stable | Stable | Stable |

[Preparation method]

1) Phase A is weighed and dissolved while heating to 85 to 95° C.

2) The result is mixed with Phase B, followed by stirring with a disper while slowly cooling from 90° C. to 55° C.

3) When the result is converted to a transparent phase at about 65 to about 58° C., it is stirred along with phase C to obtain nanoemulsion.

4) Phase D is added thereto, followed by stirring.

5) The result is cooled to 30° C., followed by vacuum defoaming to complete preparation.

TABLE 9

| Moisturizing cream | | | | |
|---|---|---|---|---|
| | Component name | Example 30 (wt %) | Example 31 (wt %) | Example 32 (wt %) |
| Phase A | Example 2 (mixed surfactant) | 8 | 10 | 15 |
| | Cetyl ethylhexanoate | 5 | 8 | 10 |
| | Ethylhexyl palmitate | 3 | 2 | 3 |
| | Argan oil | 1 | 1 | 1 |
| | Olive oil | 0.8 | 0.8 | 0.8 |
| | Tocopheryl acetate | 0.1 | 0.1 | 0.1 |
| | Camellia oil | 0.8 | 0.5 | 0.6 |
| Phase B | Glycerin | 8 | 10 | 12 |
| | Distilled water | 6 | 7 | 8 |
| Phase C | 1,3-butylene glycol | 6 | 8 | 10 |
| | 1,2-hexanediol | 2 | 2 | 2 |
| | Dipropylene glycol | 3 | 3 | 3 |
| | EDTA-2Na | 0.05 | 0.05 | 0.05 |
| | Allantoin | 0.1 | 0.1 | 0.1 |
| | Ethyl ascorbic acid | 0.5 | 0.8 | 1 |
| | Turmeric root extract | 0.1 | 0.1 | 0.1 |
| | Distilled water | 54.25 | 45.15 | 31.65 |
| | Lavender citrus fragrance | 0.1 | 0.1 | 0.1 |
| | Polyglyceryl-10 stearate/ polyglyceryl-10 oleate | 0.5 | 0.6 | 0.8 |
| | Carbomer-940 | 0.40 | 0.40 | 0.40 |
| | Transparent xanthan gum | 0.1 | 0.1 | 0.1 |
| Phase D | Bamboo extract | 0.1 | 0.1 | 0.1 |
| | Cabbage extract | 0.1 | 0.1 | 0.1 |
| | Carrot extract | 0.1 | 0.1 | 0.1 |
| | Total | 100 | 100 | 100 |
| | Appearance | High-viscosity cream | High-viscosity cream | High-viscosity cream |
| | pH | 5.56 | 5.62 | 5.78 |
| | Average particle size (nm) | 68.25 | 95.22 | 215.67 |
| | Specific gravity | 0.995 | 0.993 | 0.991 |
| | Stability (45° C., 3 months) | Stable | Stable | Stable |

[Preparation method]

1) Phase A is weighed and dissolved while heating to 85 to 95° C.

2) The result is mixed with Phase B, followed by stirring with a disper while slowly cooling from 90° C. to 55° C.

3) When the result is converted into a transparent phase at about 65 to about 58° C., Phase C is added thereto, followed by stirring to obtain a nanoemulsion.

4) Phase D is added to the nanoemulsion, followed by stirring.

5) The result is cooled to 30° C., followed by vacuum defoaming to complete preparation.

TABLE 10

| Anti-aging ampoule essence | | | | |
|---|---|---|---|---|
| | Component name | Example 33 (wt %) | Example 34 (wt %) | Example 35 (wt %) |
| Phase A | Example 2 (mixed surfactant) | 5 | 7 | 12 |
| | Cetyl ethylhexanoate | 2 | 3 | 5 |
| | Ethylhexyl palmitate | 1 | 2 | 2 |
| | Argan oil | 1 | 1 | 1 |
| | Retinol 50C | 0.0001 | 0.0001 | 0.0001 |
| | Olive oil | 0.8 | 0.8 | 0.8 |
| | Tocopheryl acetate | 0.1 | 0.1 | 0.1 |
| | Camellia oil | 0.8 | 0.5 | 0.6 |
| Phase B | Glycerin | 8 | 10 | 12 |
| | Distilled water | 6 | 7 | 8 |
| Phase C | 1,3-butylene glycol | 5 | 5 | 5 |
| | 1,2-hexanediol | 2 | 2 | 2 |
| | Dipropylene glycol | 4 | 4 | 4 |
| | Genistein | 0.1 | 0.1 | 0.1 |
| | Ascorbic acid | 0.1 | 0.2 | 0.5 |
| | Ethyl ascorbic acid | 0.5 | 0.3 | 0.2 |
| | Daidzein | 0.1 | 0.1 | 0.1 |
| | Distilled water | 62.1199 | 55.7199 | 45.4199 |
| | Lavender citrus fragrance | 0.08 | 0.08 | 0.08 |
| | Polyglyceryl-10 stearate/ polyglyceryl-10 oleate | 0.7 | 0.7 | 0.7 |
| | Carbomer-941 | 0.20 | 0.20 | 0.20 |
| | Transparent xanthan gum | 0.1 | 0.1 | 0.1 |
| Phase D | Beta-glucan | 0.1 | 0.1 | 0.1 |
| | Hibiscus extract | 0.1 | 0.1 | 0.1 |
| | Rose extract | 0.1 | 0.1 | 0.1 |
| | Total | 100 | 100 | 100 |
| | Appearance | low-viscosity fluid | low-viscosity fluid | low-viscosity fluid |
| | pH | 5.85 | 5.89 | 5.82 |
| | Average particle size (nm) | 98.85 | 147.26 | 228.51 |
| | Specific gravity | 1.001 | 0.999 | 0.998 |
| | Stability (45° C., 3 months) | Stable | Stable | Stable |

[Preparation method]

1) Phase A is weighed and dissolved while heating to 85 to 95° C.

2) The result is mixed with Phase B, followed by stirring with a disper while slowly cooling from 90° C. to 55° C.

3) When the result is converted into a transparent phase at about 65 to about 58° C., Phase C is added thereto, followed by stirring to obtain a nanoemulsion.

4) Phase D is added to the nanoemulsion, followed by stirring.

5) The result is cooled to 30° C., followed by vacuum defoaming to complete preparation.

As is apparent from the foregoing, the present invention provides a surfactant mixture of high-purity sucrose fatty acid ester and polyglyceryl-10 fatty acid ester as surfactants. A transparent microemulsion can be prepared by only simple stirring the ternary component system formed by adding an oil and purified water to the surfactant mixture. In addition, a nanoemulsion can be prepared therefrom under simple conditions.

The present invention is applicable to skin toners, lotions, creams, essences, ampoules, or mask sheets in cosmetics and can be absorbed quickly in the skin and exhibits excellent skin improvement effects such as moisturizing, fine wrinkle alleviation, whitening and lifting improvement and pH improvement.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing a mixed surfactant, the method comprising mixing sucrose distearate and polyglyceryl-10 oleate to obtain a mixture;

adjusting a pH of the mixture to 9 to 11;

allowing the mixture to react by stirring at 120 to 180° C. for 2 to 4 hours in the presence of nitrogen gas;

adjusting the pH of the mixture to 6 to 8; and cooling the mixture to 50° C. or lower to obtain the mixed surfactant, wherein the mixed surfactant is a yellow paste and has an HLB value of 10.2 to 13.2.

2. A method for preparing a nanoemulsion, the method comprising mixing the mixed surfactant prepared by the method of claim 1, with cetyl ethylhexanoate as an oil phase and heating the mixture to 68 to 85° C. to dissolve the same; and adding an aqueous phase to the heated and dissolved mixture, followed by stirring at 700 to 4,000 rpm for 2 to 8 minutes to prepare the nanoemulsion.

* * * * *